United States Patent [19]

Yamagata et al.

[11] Patent Number: 5,082,781
[45] Date of Patent: Jan. 21, 1992

[54] β-AMYLASE GENE

[75] Inventors: Hideo Yamagata; Noriyuki Kitamoto, both of Nagoya; Takeo Kato, Aichi; Norihiro Tsukagoshi; Shigezo Udaka, both of Nagoya, all of Japan

[73] Assignee: Shigezo Udaka, Nagoya, Japan

[21] Appl. No.: 611,480

[22] Filed: Nov. 9, 1990

Related U.S. Application Data

[63] Continuation of Ser. No. 315,129, Feb. 24, 1989, abandoned.

[30] Foreign Application Priority Data

Feb. 26, 1988 [JP] Japan .................................. 63-43708

[51] Int. Cl.$^5$ ...................... C12N 9/26; C12N 15/56; C12N 15/75; C12N 1/21; C12N 1/00
[52] U.S. Cl. ................................. 435/201; 435/252.3; 435/252.31; 435/320.1; 536/27
[58] Field of Search ............ 536/27; 435/320.1, 172.3, 435/69.1, 201, 252.3, 252.31

[56] References Cited

U.S. PATENT DOCUMENTS

| | | | |
|---|---|---|---|
| 4,469,791 | 9/1984 | Colson et al. | 435/253 |
| 4,529,695 | 7/1985 | Weisblum | 435/69.1 |
| 4,647,538 | 3/1987 | Zeikus et al. | 435/201 |

FOREIGN PATENT DOCUMENTS

| | | |
|---|---|---|
| 034470 | 8/1981 | European Pat. Off. . |
| 120693 | 10/1984 | European Pat. Off. . |
| 8601832 | 3/1986 | PCT Int'l Appl. . |

OTHER PUBLICATIONS

Biosis Database, Abstract No. 87037025, N. Kitamo et al., "Cloning and Sequencing of the Gene Encoding Thermophilic Beta Amylase of Clostridium-Thermosulfurogenes" & J. of Bacteriology (US), vol. 170, No. 12, 1988, pp. 5848–5854.

Biosis Database, Abstract No. 35038111, L. Bhatnagar et al., "Cloning of Beta Amylase From Clostridium--Thermosulfurogenes Strain 4B", & Abstracts of the Annual Meeting of the American Society for Microbiology, vol. 88, No. 0, 1988, p. 211.

Chemical Abstracts, vol. 103, No. 1, Jul. 8, 1985, Abstract No. 2663n, Columbus, Ohio, H. H. Hyun et al., "General Biochemical Characterization of Thermostable Extracellural . . . " & Appl. Environ. Microbiol., vol. 49, No. 5, 1989, pp. 1162–1167.

Chemical Abstracts, vol. 108, No. 5, Feb. 1, 1988, Abstract No. 36267e, Columbus, Ohio, Badal C. Saha et al., "Behavior of A Novel Thermostable Beta-Amylase on Raw Starch" & Enzyme Microb. Technol., vol. 9, No. 10, 1987, pp. 598–601.

Chemical Abstracts, vol. 109, No. 19, Nov. 7, 1988, Abstract No. 166194k, Columbus, Ohio, Gwo Jenn Shen et al., "Purification and Characterization of A Novel Thermostable Beta-Amylase From Clostridium . . . ", vol. 254, No. 3, 1988, pp. 835–840.

Primary Examiner—Richard A. Schwartz
Assistant Examiner—S. L. Nolan
Attorney, Agent, or Firm—Oblon, Spivak, McClelland, Maier & Neustadt

[57] ABSTRACT

A novel β-amylase gene is provided. This gene is useful for production of a thermophilic β-amylase obtained from *Clostridium thermosulfurogenes* on a large scale, especially from genetically engineered microorganisms introduced with this gene. *B. subtilis* was transformed with a plasmid pNK1 containing the above gene and the transformed *B. subtilis* cells produced β-amylase having the same thermostability as that of β-amylase obtained from *C. thermosulfurogenes*.

19 Claims, 8 Drawing Sheets

FIG.1-1

```
* 318                                                                  377*
TTT.CTA.CTT.CTT.GGC.ACA.GAG.AAA.ATT.AGT.CAC.AGC.TAT.AAT.AGC.TGG.TGC.TGT.AAA.GCA

* 378                                                                  437*
GTA.GGT.AAA.GCA.AAA.TTA.TAG.TTA.GGA.GGT.GAT.ATT.AAA.ATA.GAA.ATT.TGA.TAG.AAA.CTG

* 438                                                                  497*
AAT.ATA.ATT.ATT.GAA.AGG.GGT.GGG.AAC.TAT.TGG.CAA.AAT.AAT.ATC.TTA.TTA.AAA.TTT.TTG

* 498                                                                  557*
GCG.GCA.AAA.AAT.AGT.GAT.TAT.ATT.ATT.TTT.ATC.GTA.TGA.TGG.GAG.GGA.AAA.TAA.AAA.TAG

* 558                                                                  617*
ATG.ATT.GGA.GCT.TTT.AAA.AGG.TTG.GGT.CAA.AAA.TTG.TTT.TTG.ACA.TTG.TTA.ACG.GCA.TCA
MET-Ile-Gly-Ala-Phe-Lys-Arg-Leu-Gly-Gln-Lys-Leu-Phe-Leu-Thr-Leu-Leu-Thr-Ala-Ser

* 618                                                                  677*
TTA.ATT.TTT.GCA.TCT.TCT.ATA.GTA.ACT.GCT.AAT.GCA.AGC.ATA.GCA.CCA.AAT.TTC.AAA.GTT
Leu-Ile-Phe-Ala-Ser-Ser-Ile-Val-Thr-Ala-Asn-Ala-Ser-Ile-Ala-Pro-Asn-Phe-Lys-Val

* 678                                                                  737*
TTT.GTA.ATG.GGT.CCA.TTA.GAA.AAA.GTC.ACA.GAT.TTC.AAA.GAT.CAA.TTG.ATA
Phe-Val-MET-Gly-Pro-Leu-Glu-Lys-Val-Thr-Asp-Phe-Lys-Asp-Gln-Leu-Ile

* 738                                                                  797*
ACT.TTA.AAG.AAT.AAT.GGT.GTT.TAT.GGT.ATA.ACA.ACA.GAT.ATT.TGG.TGG.GGC.TAT.GTT.GAA
Thr-Leu-Lys-Asn-Asn-Gly-Val-Tyr-Gly-Ile-Thr-Thr-Asp-Ile-Trp-Trp-Gly-Tyr-Val-Glu

* 798                                                                  857*
AAT.GCA.GGT.GAA.AAT.CAA.TTT.GAC.TGG.AGT.TAT.TAT.AAG.ACA.TAT.GCT.GAT.ACC.GTA.CGC
Asn-Ala-Gly-Glu-Asn-Gln-Phe-Asp-Trp-Ser-Tyr-Tyr-Lys-Thr-Tyr-Ala-Asp-Thr-Val-Arg
```

FIG.1-2

```
* 858                                                                                              917*
GCT.GCG.GGA.TTG.AAG.TGG.GTT.CCA.ATA.ATG.TCA.ACG.CAT.GCC.TGT.GGA.GGT.AAT.GTT.GGT
Ala-Ala-Gly-Leu-Lys-Trp-Val-Pro-Ile-MET-Ser-Thr-His-Ala-Cys-Gly-Gly-Asn-Val-Gly

* 918                                                                                              977*
GAT.ACA.GTA.AAT.ATA.CCT.ATT.CCG.TCA.TGG.GTA.TGG.ACA.AAA.GAT.ACC.CAA.GAT.AAT.ATG
Asp-Thr-Val-Asn-Ile-Pro-Ile-Pro-Ser-Trp-Val-Trp-Thr-Lys-Asp-Thr-Gln-Asp-Asn-MET

* 978                                                                                             1037*
CAG.TAT.AAG.GAT.GAA.GCC.GGA.AAT.TGG.GAT.AAT.GAA.GCA.GTA.AGT.CCA.TGG.TAT.TCT.GGC
Gln-Tyr-Lys-Asp-Glu-Ala-Gly-Asn-Trp-Asp-Asn-Glu-Ala-Val-Ser-Pro-Trp-Tyr-Ser-Gly

* 1038                                                                                            1097*
TTA.ACC.CAA.CTC.TAT.AAT.GAA.TTT.TAT.TCA.TCT.TTT.GCA.TCA.AAT.TTT.AGC.AGC.TAT.AAA
Leu-Thr-Gln-Leu-Tyr-Asn-Glu-Phe-Tyr-Ser-Ser-Phe-Ala-Ser-Asn-Phe-Ser-Ser-Tyr-Lys

* 1098                                                                                            1157*
GAT.ATA.ATT.ACT.AAA.ATA.TAT.ATA.TCT.GGA.GGC.CCT.TCT.GGA.GAA.TTA.AGA.TAT.CCT.TCA
Asp-Ile-Ile-Thr-Lys-Ile-Tyr-Ile-Ser-Gly-Gly-Pro-Ser-Gly-Glu-Leu-Arg-Tyr-Pro-Ser

* 1158                                                                                            1217*
TAT.AAT.CCT.TCG.CAT.GGA.TGG.ACA.TAT.CCT.GGA.CGT.GGC.TCG.CTG.CAG.TGC.TAT.AGT.AAA
Tyr-Asn-Pro-Ser-His-Gly-Trp-Thr-Tyr-Pro-Gly-Arg-Gly-Ser-Leu-Gln-Cys-Tyr-Ser-Lys

* 1218                                                                                            1277*
GCG.GCT.ATA.ACA.AGT.TTT.CAA.AAT.GCT.ATG.AAG.TCT.AAA.TAT.GGA.ACT.ATA.GCA.GCA.GTT
Ala-Ala-Ile-Thr-Ser-Phe-Gln-Asn-Ala-MET-Lys-Ser-Lys-Tyr-Gly-Thr-Ile-Ala-Ala-Val

* 1278                                                                                            1337*
AAT.AGT.GCA.TGG.GGT.ACA.AGC.CTA.ACT.GAT.TTT.TGT.CAA.ATT.AGT.CCA.CCT.ACA.GAT.GGT
Asn-Ser-Ala-Trp-Gly-Thr-Ser-Leu-Thr-Asp-Phe-Cys-Gln-Ile-Ser-Pro-Pro-Thr-Asp-Gly

* 1338                                                                                            1397*
GAT.AAT.TTC.TTT.ACA.AAT.GGT.TAT.AAA.ACT.ACT.TAT.AAA.GAC.TTT.TTG.ACA.TGG.ACA.TAT
Asp-Asn-Phe-Phe-Thr-Asn-Gly-Tyr-Lys-Thr-Thr-Tyr-Lys-Asp-Phe-Leu-Thr-Trp-Thr-Tyr
```

FIG.1-3

```
* 1398                                                                      1457*
CAA.AGT.GTT.TTG.ACT.AAT.GAG.TTA.GCC.AAT.ATT.GCT.TCT.GTA.GCT.CAT.AGC.TGC.TTT.GAT
Gln-Ser-Val-Leu-Thr-Asn-Glu-Leu-Ala-Asn-Ile-Ala-Ser-Val-Ala-His-Ser-Cys-Phe-Asp

* 1458                                                                      1517*
CCA.GTA.TTT.AAT.GTT.CCA.ATA.GGA.GCA.AAA.ATA.GCT.GGA.GTG.CAT.TGG.CTA.TAT.AAT.AGT
Pro-Val-Phe-Asn-Val-Pro-Ile-Gly-Ala-Lys-Ile-Ala-Gly-Val-His-Trp-Leu-Tyr-Asn-Ser

* 1518                                                                      1577*
CCG.ACA.ATG.CCA.CAT.GCT.GCA.GAA.TAT.TGT.GCC.GGT.TAT.TAT.AAT.TAT.AGC.ACG.CTA.CTC
Pro-Thr-MET-Pro-His-Ala-Ala-Glu-Tyr-Cys-Ala-Gly-Tyr-Tyr-Asn-Tyr-Ser-Thr-Leu-Leu

* 1578                                                                      1637*
GAT.CAA.TTT.AAG.GCA.TCT.AAT.CTT.GCT.ATG.ACA.TTT.ACA.TGT.CTT.GAA.ATG.GAT.GAT.TCT
Asp-Gln-Phe-Lys-Ala-Ser-Asn-Leu-Ala-MET-Thr-Phe-Thr-Cys-Leu-Glu-MET-Asp-Asp-Ser

* 1638                                                                      1697*
AAT.GCA.TAT.GTA.AGT.CCA.TAT.TAT.TCT.GCA.CCT.ATG.ACG.TTA.GTC.CAT.TAT.GTA.GCT.AAT
Asn-Ala-Tyr-Val-Ser-Pro-Tyr-Tyr-Ser-Ala-Pro-MET-Thr-Leu-Val-His-Tyr-Val-Ala-Asn

* 1698                                                                      1757*
CTT.GCT.AAT.AAT.AAA.GGT.ATA.GTC.CAC.AAT.GGA.GAA.AAT.GCT.TTG.GCT.ATA.TCC.AAC.AAC
Leu-Ala-Asn-Asn-Lys-Gly-Ile-Val-His-Asn-Gly-Glu-Asn-Ala-Leu-Ala-Ile-Ser-Asn-Asn

* 1758                                                                      1817*
AAT.CAA.GCT.TAT.GTG.AAT.TGT.GCA.AAT.GAA.TTA.ACA.GGA.TAT.AAT.TTT.TCT.GGA.TTT.ACA
Asn-Gln-Ala-Tyr-Val-Asn-Cys-Ala-Asn-Glu-Leu-Thr-Gly-Tyr-Asn-Phe-Ser-Gly-Phe-Thr

* 1818                                                                      1877*
CTT.TTA.AGA.CTT.TCG.AAT.ATT.GTA.AAT.AGT.GAT.GGA.TCT.GTG.ACA.TCA.GAG.ATG.GCT.CCT
Leu-Leu-Arg-Leu-Ser-Asn-Ile-Val-Asn-Ser-Asp-Gly-Ser-Val-Thr-Ser-Glu-MET-Ala-Pro

* 1878                                                                      1937*
TTT.GTA.ATT.AAT.ATA.GTT.ACA.CTA.ACG.CCT.AAC.GGT.ACG.ATA.CCA.GTT.ACA.TTT.ACA.ATA
Phe-Val-Ile-Asn-Ile-Val-Thr-Leu-Thr-Pro-Asn-Gly-Thr-Ile-Pro-Val-Thr-Phe-Thr-Ile
```

FIG.1-4

```
* 1938                                                                                              1997*
AAC.AAT.GCG.ACA.ACT.TAT.TAT.GGA.CAA.AAT.GTA.TAT.ATT.GTT.GGT.AGT.ACA.TCT.GAT.CTT
Asn-Asn-Ala-Thr-Thr-Tyr-Tyr-Gly-Gln-Asn-Val-Tyr-Ile-Val-Gly-Ser-Thr-Ser-Asp-Leu

* 1998                                                                                              2057*
GGA.AAT.TGG.AAT.ACA.ACC.TAT.GCC.CGT.GGT.CCT.GCA.TCA.TGC.CCT.AAT.TAT.CCT.ACT.TGG
Gly-Asn-Trp-Asn-Thr-Thr-Tyr-Ala-Arg-Gly-Pro-Ala-Ser-Cys-Pro-Asn-Tyr-Pro-Thr-Trp

* 2058                                                                                              2117*
ACA.ATA.ACG.CTT.AAT.CTA.TTA.CCT.GGT.GAG.CAG.ATA.CAG.TTT.AAA.GCT.GTA.AAA.ATT.GAT
Thr-Ile-Thr-Leu-Asn-Leu-Leu-Pro-Gly-Glu-Gln-Ile-Gln-Phe-Lys-Ala-Val-Lys-Ile-Asp

* 2118                                                                                              2177*
AGT.TCA.GGA.AAT.GTA.ACT.TGG.GAA.GGT.GGC.TCG.AAT.CAT.ACT.TAT.ACT.GTG.CCG.ACA.TCT
Ser-Ser-Gly-Asn-Val-Thr-Trp-Glu-Gly-Gly-Ser-Asn-His-Thr-Tyr-Thr-Val-Pro-Thr-Ser

* 2178                                                                                              2237*
GGG.ACT.GGT.AGT.GTC.ACC.ATT.ACA.TGG.CAA.AAT.TAA.TCA.ATA.AAA.TGT.TAC.ACA.TAG.AAC
Gly-Thr-Gly-Ser-Val-Thr-Ile-Thr-Trp-Gln-Asn-***

* 2238                                                                                              2297*
AAA.TTG.TAA.ACA.CTG.GAA.TAT.ATT.CCG.GTG.TTT.TTT.TGT.ATA.TTA.TGG.GCG.TTT.AAT.GTT

* 2298                                                                                              2357*
AAA.AAT.AAT.AGT.GTT.TTG.ATT.TTA.TTA.AAA.AGT.TTG.GAG.GTA.AGA.GAT.GAG.TAA.AAA.AGT

* 2358                                                                                              2417*
TGG.TAT.TCC.AAA.AGG.GCT.TTT.ATA.CTA.CAA.CTT.TTA.TCC.TAT.GTG.GAA.AAC.ATT.TTT.TGA
```

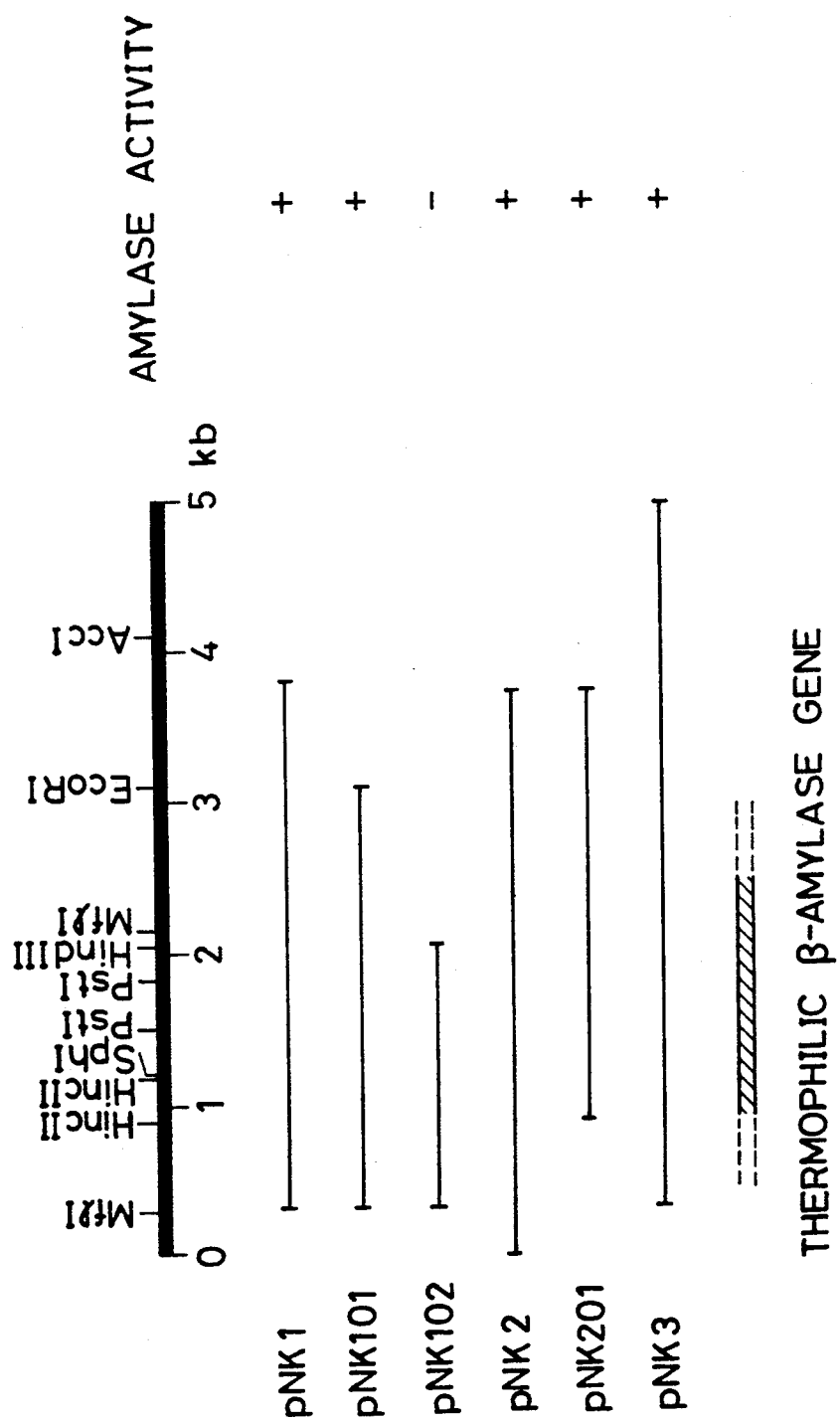

β-AMYLASE GENE

This application is a continuation of application Ser. No. 07/315,129, filed on Feb. 24, 1989, now abandoned.

BACKGROUND OF THE INVENTION

1. Field of the Invention

The present invention relates to a novel β-amylase gene.

2. Description of the Prior Art

β-amylase is an enzyme acting on starch to cut the α-1,4-glucoside bond from the non-reducing terminal into a maltose unit and form β-maltose. Not many microorganisms are known to produce β-amylase, and in industry there is used a β-amylase derived from soybean which has an optimal temperature of about 60° C.

*Clostridium thermosulfurogenes* is a thermophilic obligate anaerobe with high starch decomposition ability and extracellularly secretes thermophilic β-amylase (Japanese Patent Disclosure No. 62-500422). This thermophilic β-amylase has an optimum temperature of 75° C. and is stable to heat even at 85° C. Although the optimum pH thereof ranges from 5.5 to 6.0, the thermophilic β-amylase is stable in the pH range of from 3.5 to 6.5. Further, this β-amylase is an SH enzyme which is inactivated with SH reagents such as PCMB (parachloromercuribenzoate), iodo acetate, $Cu^{2+}$ and $Hg^{2+}$. Among these properties, the thermostability is particularly superior to that of the β-amylase derived from soybean and other sources. It is expected that the thermophilic β-amylase from *Clostridium thermosulfurogenes* will be a very useful enzyme for industrial production of maltose and other sugars from starch.

SUMMARY OF THE INVENTION

Accordingly, an object of the present invention is to provide a gene coding the above thermophilic β-amylase, which is indispensable for the production of thermophilic β-amylase obtained from *Clostridium thermosulfurogenes* on a large scale, and genetically engineered microorganisms harboring this gene.

The aforementioned object of the invention can effectively be accomplished by providing a β-amylase gene comprising a base sequence which has 70% or more homology on the basis of the amino acid sequence with the β-amylase gene base sequence which is a part of the base sequence described in FIG. 1 starting from the base No. 654 to the base No. 2211.

BRIEF EXPLANATION OF THE DRAWINGS

FIG. 1 shows base sequence (A) of the present invention, anterior and posterior base sequences to the sequence (A) and an amino acid sequence corresponding to the base sequence (A).

FIG. 4 shows a subcloning of the thermophilic β-amylase gene.

Figure 2:
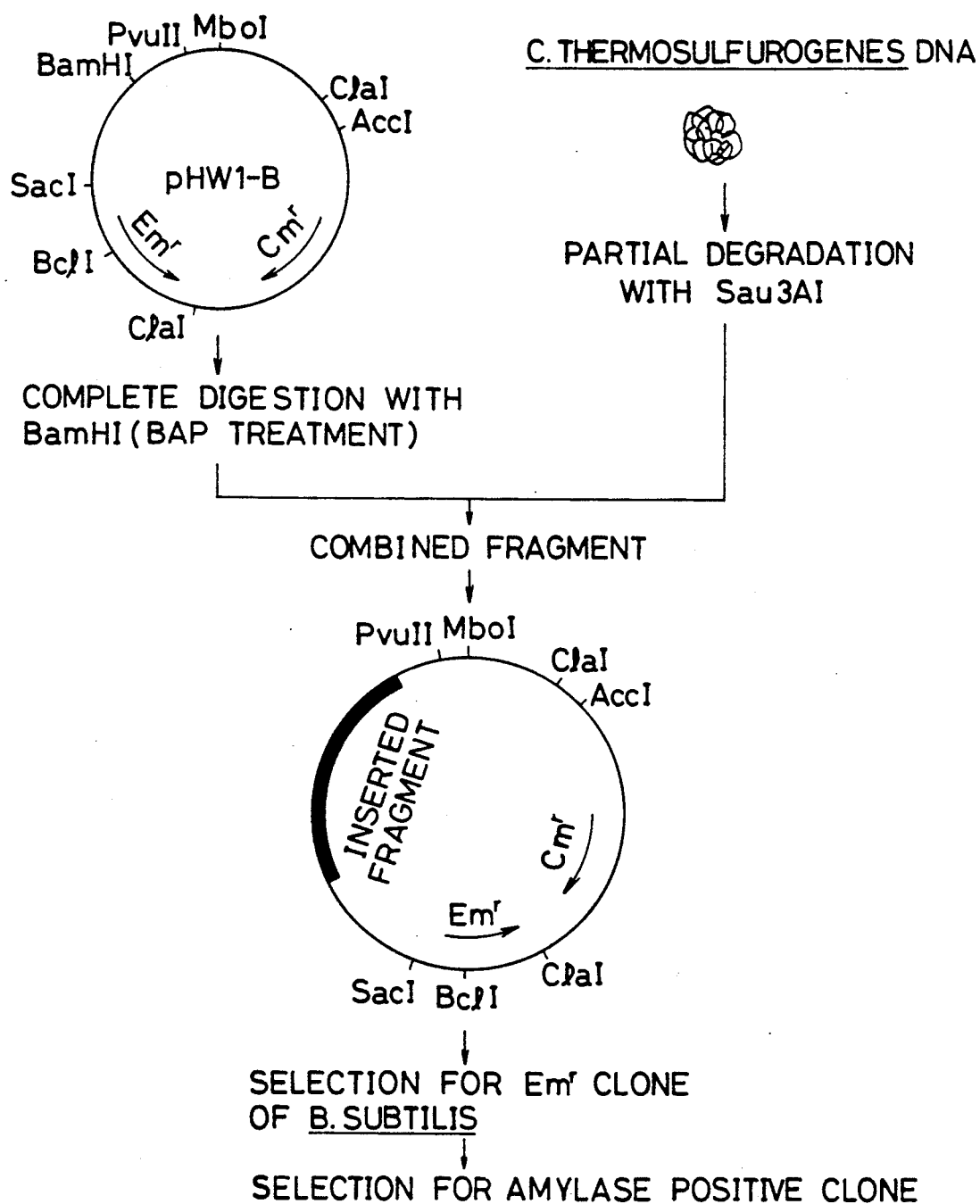
FIG. 2 shows a flow sheet of a shotgun cloning method for the thermophilic β-amylase gene of *C. thermosulfurogenes*.

The thermophilic β-amylase gene of the present invention will now be explained in detail.

The thermophilic β-amylase gene of the present invention includes a base sequence corresponding to an amino acid sequence coded by a 1557 bp base sequence (hereinafter referred to as the base sequence (A)) which is a part of the base sequence in FIG. 1 starting from the base No. 654 "A" and ending at the base No. 2211 "C", and the base sequences corresponding to the amino acid sequences having 70% or more homology to the amino acid sequence coded by the base sequence (A). An amino acid sequence having the β-amylase activity of the thermophilic β-amylase obtained by use of the base sequence (A) can be obtained by using the base sequence corresponding to the amino acid sequence having 70% or more homology to the amino acid sequence coded by the base sequence (A). This is clearly supported by a report regarding "Homology between α-amylases" in J. Jpn. Soc. Starch Sci., Vol. 33, No. 2, 112-118 (1986).

A process for preparation of the gene of the present invention shown in FIG. 1 will now be explained.

(1) Strain, Plasmid and Phage (*Clostridium thermosulfurogenes* ATCC 33733, *Bacillus subtilis* 1A289 (amyE sacA321 aro1906 metB5) and *Escherishia coli* JM103 [supE thi Δ(lac-proAB) (F' tanD36 proAB lacI⁹Z ΔM15], MV1184 [ara Δ(lac-pro) strA thi (φ80 ΔlacIZ ΔM15)Δ(srl-recA)306::Tn10 (tetr)F':traD36 proAB lacI⁹Z ΔM15] were used as a strain. *E. coli* JM103 and MV1184 were used as hosts for plasmid pUC118, and pUC119 (Ap, 3.3 kb), and M13 mp18 and mp19. M13K07 was used as a helper phage in preparation of a single stranded DNA from pUC118 and pUC119. Further pHW1-B(Cm', Em' 4.4 kb) was used as a cloning plasmid vector for *B. subtilis*.

(2) Composition of Culture Medium and Cultivating Condition

*C. thermosulfurogenes* was subjected to a stationary culture using a TYE medium containing 1.0% starch (see Table 1) at 60° C. under an anaerobic condition. *B. subtilis* was subjected to a shaking culture using an antibiotic medium 3 (Difco) at 37° C. *E. coli* was subjected to a shaking culture using a L medium (5 g tryptone, 10 g yeast extract, 5 g NaCl, $H_2O$ 1l, pH 7.6) and 2×YT medium (16 g tryptone, 10 g yeast extract, 5 g NaCl, $H_2O$ 1 l) at 37° C. 50 μg/ml ampycilin (Ap) and 10 μg/ml erythromycin (Em) were optionally added to the media.

TABLE 1

| Composition of TYE medium | |
|---|---|
| Tryptone | 10 g |
| Yeast extract | 3 g |
| NH₄Cl | 1 g |
| MgCl₂.6H₂O | 0.2 g |
| KH₂PO₄ | 0.3 g |
| Na₂PO₄.7H₂O | 2 g |
| Inorganic compounds solution* | 10 ml |
| 2.5% FeSO₄ | 0.3 ml |
| 0.2% resazurin | 1 ml |
| Vitamins solution** (sterillized) | 5 ml |
| 2.5% Na₂S | 20 ml |
| H₂O | 1 l |
| Nitrilotriacetate (adjusted with KOH at pH 6.5) | 1.28 mg |
| FeSO₄.7H₂O | 10 mg |
| MnCl₂.4H₂O | 10 mg |
| CoCl₂.6H₂O | 16 mg |
| CaCl₂.2H₂O | 10 mg |
| ZnCl₂ | 10 mg |
| CuCl₂ | 2 mg |
| H₃BO₃ | 1 mg |
| NaMoO₄.2H₂O | 1 mg |
| Nickel acetate | 2.6 mg |

TABLE 1-continued

| Composition of TYE medium | |
|---|---|
| biotin | 0.1 mg |
| folic acid | 0.1 mg |
| pyridoxine.HCl | 0.5 mg |
| riboflavin | 0.25 mg |
| thiamin | 0.25 mg |
| nicotinic acid | 0.25 mg |
| pantothenic acid | 0.25 mg |
| V-B$_{12}$ | 5 µg |
| p-aminobenzoic acid | 0.25 mg |
| thioctic acid | 0.25 mg |
| H$_2$O | 50 ml |

*Inorganic compounds solution
**Vitamins solution

(3) Preparation of DNA

A chromosome DNA of *C. thermosulfurogenes* was prepared by a Tris-SDS method described in Saito, Miura et al., Biochim. Biophys. Acta, 72, 619 (1963). Plasmid DNAs were prepared respectively by the Birnboim-Doly's method [Nucleic acids Res., 7, 1513 (1979)] from *E. coli* and by the method of Tanaka et al. [J. Bacteriol., 129, 1487(1977)] from *B. subtilis*.

A single stranded plasmid DNA for determination of a base sequence was prepared on the basis of the method of J. Messing et al. [Methods Enzymol., 101, 20(1983] by using a helper phage M13K07. Further a single stranded phase DNA was prepared by a commonly used method.

(4) Cloning of thermophilic β-amylase gene from *C. thermosulfurogenes*

The chromosome DNA of *C. thermosulfurogenes* was partially cleaved with a restriction enzyme Sau 3A1. The cleaved DNA was subjected to an agarose gel electrophoresis and 3 kb-9 kb fragments were eluted electrically and collected from the agarose gel. The collected fragments were purified by treatment with phenol-chloroform. The resulting fragments of about 0.3 µg were cleaved completely with Bam H1 and combined with a plasmid pHW1-B (about 0.1 µg) which had previously been treated with a bacterial alkaline phosphatase by using a T4 DNA ligase. Then *B. subtilis* was transformed by use of the resulting ligation reaction mixture on the basis of a protoplast transformation procedure of Cohen et al. [Mol. Gen. Genet. 168, 111(1979)].

The following strain was found as a thermophilic β-amylase producing strain: A strain forming a halo around its colony by staining with 10 mM I$_2$-KI solution after proliferation on a M3 plate containing 10 µg/1 of Em and 0.3% of starch for a day and incubation at 65° C. for 3 hours.

(5) Method for Measuring β-Amylase Activity

The supernant fluid of the culture was saturated with 80% ammonium sulfate to obtain precipitate. The precipitate was dissolved in about 5 ml of a 50 mM acetate buffer solution (pH 6.0) and subjected to dialysis against 2 l of the 50 mM acetate buffer solution (pH 6.0) for 24 hours to obtain a crude enzyme solution.

Measurement of the β-amylase activity was conducted as follows: The crude enzyme solution was added to a 0.5% starch −50 mM acetate buffer solution and the resultant mixture was maintained at 65° C. for 30 minutes to react the enzyme with starch. Amount of produced maltose was calculated as a reducing sugar from the absorbancy at a wavelength of 530 nm on the basis of the DNS method [Murao et al. Agric. Biol. Chem., 43, 719(1979)].

Decomposition products of starch were detected by staining, by a silver nitrate-sodium hydroxide method, sugars separated by paper chromatography (developing solvent: 70% n-propanol). Bands in the SDS-polyacrylamide gel were detected by an active staining method.

(6) Southern Hybridization

DNA fragments about 2 µg used for a probe were labeled on the basis of a nick translation method by using *E. coli* polymerase I in the presence of α$^{32}$P-dCTP to form a DNA probe with a high specific radioactivity. A chromosome DNA of *C. thermosulfurogenes* used for hybridization was cleaved with EcoRI, EcoRI+BglII, EcoRI+BamI or BamI, and then subjected to 0.7% agarose gel electropholesis. The cleaved chromosome DNA in the agarose gel was degenerated and transferred onto a Biodyne A membrane to fix the degenerated DNA to the membrane. Hybridization was conducted between the resulting membrane and a probe which had previously been prepared, and then an autoradiograph was prepared.

(7) Analysis of DNA Base Sequence

A DNA fragment (about 3.6 kb) of a plasmid pNK 1 containing the thermophilic β-amylase gene of *C. thermosulfurogenes* was cleaved with MflI to form two DNA fragments having about 1.8 kb and these fragments were subcloned as pUC118 and pUC119. Determination of a base sequence in the direction from 5' to 3' was carried out as follows: The resulting inserted fragments of the plasmid were cleaved with an exonuclease III, then the cleaved fragments were treated with Klenow's fragment to change the ends thereof to blunt ends and the treated fragments were subjected to ligation to transform *E. coli*. A plasmid was prepared from the resulting transferred cell and cleaved with suitable restriction enzymes. The cleaved plasmid was subjected to agarose gel electropholesis to investigate the size of inserted DNA fragments and many clones containing shorter β-amylase gene which were deleted from its 5' end with the average intervals of 150–200 bp were selected. A single stranded DNA was prepared from the selected clones and subjected to sequencing.

Determination of the base sequence in direction from 3' to 5' was conducted as follows: DNA fragments with suitable size prepared by using restriction sites found during the procedures of the above sequencing were cloned in pUC118, pUC119, M13mp18 and M13mp19 to investigate the sequence of the DNA.

The base sequence were determined by using α$^{32}$P-dCTP on the basis of the dideoxy method [Sanger et al., Proc. Natl. Acad. Sci. USA, 74, 5463 (1977)].

(8) Cloning of the Thermophilic β-Amylase Gene of *C. thermosulfurogenes* to *B. subtilis*.

A DNA library of *C. thermosulfurogenes* was prepared by using *B. subtilis* 1A289 on the basis of the cloning method shown in FIG. 1 to obtain about 6000 transformed cells exhibiting Em$^r$. Among these, three cells exhibiting amylase - positive character were obtained. These three cells stably maintain their plasmids even on M3 - Em plates.

Soluble starch was cleaved at 65° C. for 1 hour by using crude enzyme solutions obtained from culture supernatants of these three amylase - positive cells. Then the resulting products were investigated by paper chromatography and it was found that only maltose was contained in the products. Further, the crude enzyme solutions obtained from culture supernatants of *C. thermosulfurogenes* and the three amylase - positive cells were subjected to SDS-polyacrylamide gel electropholesis and active staining. As a result, enzymatically active bands were detected at the same distances on each gel. On the basis of these results, the three amylase - positive cells were considered to secrete extracellularly thermophilic β-amylases having the same molecular weight as that of the thermophilic β-amylase of *C. thermosulfurogenes*, indicating that the complete cloning of the thermophilic β-amylase gene of *C. thermosulfurogenes* was achieved.

Figure 3A:
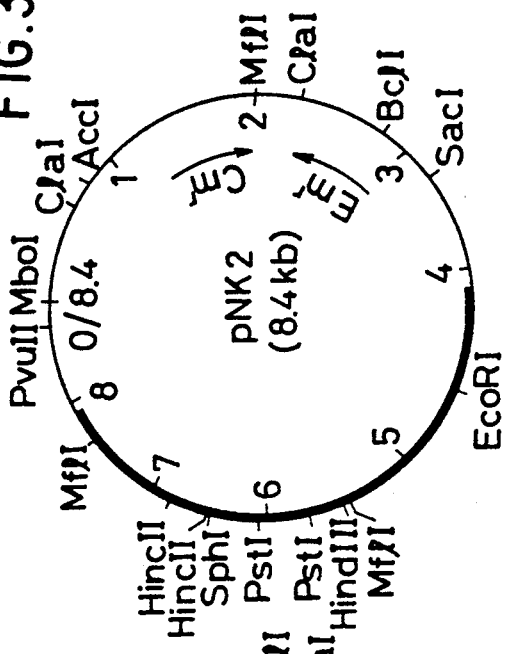
FIGS. 3A, B, and C show restriction enzyme maps of pNK1, pNK2 and pNK3.
Figure 3B:
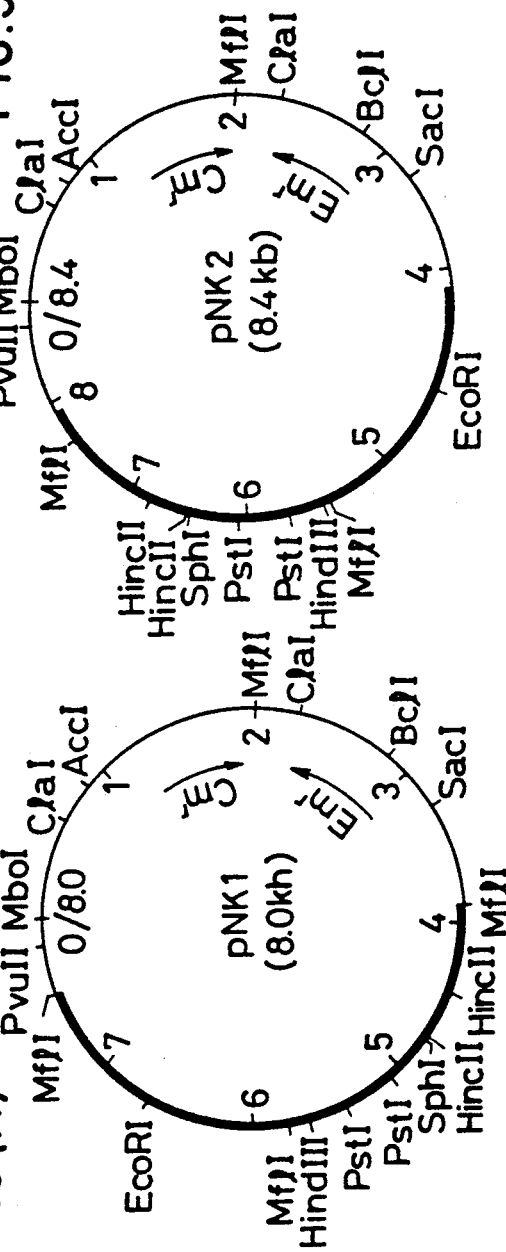
Figure 3C:
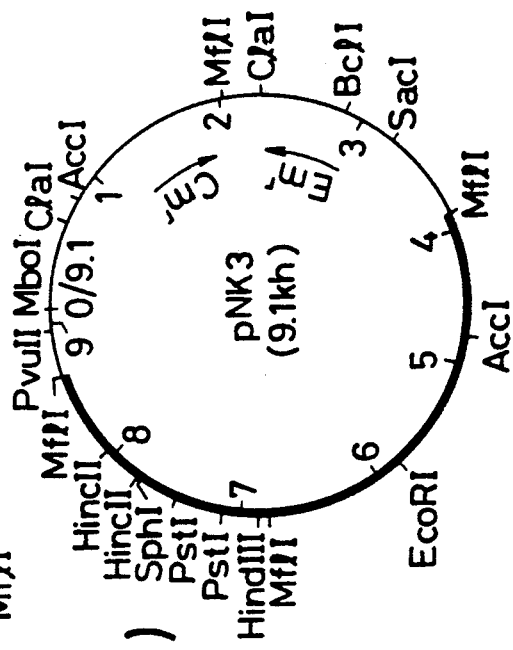

Restriction maps of plasmids pNK1, pNK2 and pNK3 contained in the three thermophilic β-amylase producing cells were constructed and shown in FIG. 3. In these plasmids, about 3.6 kb, about 4.0 kb and about 4.7 kb DNA fragments were inserted into a plasmid pHW1-B and about 3.5 kb DNA fragments were found to be present in every fragment from the comparison of the restriction maps. The insertion direction of DNA fragments were different between pNK1 and pNK2 and 3, and this difference seems to have an effect on the degree of expression of the thermophilic β-amylase activity. Further, from the analysis of some deleted plasmids prepared from the three plasmids, the thermophilic β-amylase gene was considered to be coded on an about 2.2 kb HincII-EcoRI fragment (FIG. 4).

(9) Determination of Whole DNA Base Sequence of Thermophilic β-Amylase from *C. thermosulfurogenes*

The whole DNA sequence was determined on an inserted DNA fragment (about 3.6 kb) of the plasmid pNK1 which is contained in the cell exhibiting the strongest thermophilic β-amylase activity among the three thermophilic β-amylase producing cells. As a result, the inserted DNA fragment was found to consist of 3642 bp. Detection of an open reading frame (ORF) of this 3642 bp fragment was conducted and two ORF's were found. In the direction from 5' to 3', one ORF was 1653 bp, starting from ATG of No. 558 and ended at TAA of No. 2211. The other ORF was 933 bp, starting from ATG of No. 2344 and ended at TAG of No. 3277. Among these ORF's, the ORF of 1653 bp was considered to code the thermophilic β-amylase gene on the basis of the analysis of the deleted plasmids. This 1653 bp ORF was found to code a protein consisting of 551 amino acids and having 60546 of molecular weight (FIG. 1). It is considered that a signal peptide consisting of about 30 amino acids residual group is present on the basis of the facts that the thermophilic β-amylase of *C. thermosulfurogenes* having about 56000 of molecular weight has been secreted extracellularly and that an amino acid sequence neighboring the N terminal of the protein consists of hydrophobic amino acids. In fact, the signal peptide was found to code an enzyme protein consisting of 519 amino acids starting from AGC of No. 654 from the determination of the N terminal amino acid sequence (13 amino acids) of the secreted β-amylase. From results of hydropathy test, the enzyme protein was totally hydrophilic. This protein contains 7 cysteines among 519 amino acids, and this high content of cysteine is considered to be a reason for making thermophilic the β-amylase of *C. thermosulfurogenes*.

The G+C contents of the ORF is 35.4% which is quite similar to that of *C. thermosulfurogenes* (32.6%).

A base sequence GGGAGGG which seems to be a SD sequence is present at 12 bp upper stream of the 1653 bp ORF and some base sequences similar to the promoter sequences (TTGACA . . . about 17 bp . . . TATAAT) are present at an upper stream position of the sequence GGGAGGG. An inverted repeat is present from No. 2245 to No. 2270 at the 31 bp downstream of the stop codon TAA and the inverted repeat is expected to work as a terminator since it forms a stable palindrome structure with an energy ($\Delta G$) of $-19.5$ kcal/mol.

A 309 bp fragment from No. 296 to No. 605 containing the N-terminal and a 117 bp fragment from No. 2148 to No. 2264 containing the C-terminal, both fragments being labeled with a radio-isotope, were hybridized as probes with the chromosome DNA's of *C. thermosulfurogenes* which were cleaved with EcoRI, EcoRI+Bgl II, EcoRI+BamHI or BamHI and fixed on a Biodyne A membrane. As a result, it was shown that the whole thermophilic β-amylase of *C. thermosulfurogenes* was cloned since DNA bands hydridizing with the two probes appeared at the same position.

Various microorganisms (such as yeast, fungi, bacteria and algae), animal cells and plant cells can be transformed with the plasmid containing the gene of the present invention.

The present invention will now be explained with reference to an example as follows.

EXAMPLE

*B. subtilis* 1A289 was transformed by using a plasmid pNK1 which contained the thermophilic β-amylase gene of *C. thermosulfurogenes* on the basis of a protoplast transforming method [Cohen et al., Mol. Gen. Genet., 168, 111(1979)]. The resulting transformed cell was subjected to shaking culture at 37° C. for 48 hours with 0.5 l of antibiotics medium 3 (Difco). The resulting supernatant fluid was saturated with 80% ammonium sulfate to obtain the precipitate, and the precipitate was dissolved in about 5 ml of 50 mM acetate buffer solution (pH 6.0) and was subjected to dialysis against 2 l of the 50 mM acetate buffer solution (pH 6.0) for 24 hours to obtain a crude enzyme solution. Then the β-amylase activity of the crude enzyme solution was measured. The crude enzyme solution was added to a 0.5% starch - 50 mM acetate buffer solution and the resulting mixture was maintained at 65° C. for 30 minutes to react the enzyme with starch. Then the absorbancy at the wavelength of 530 nm was measured and converted into the amount of reducing sugar on the basis of a DNS method reported by Murao et al. to obtain the amount of produced maltose. 15 mg of the thermophilic β-amylase were obtained from this culture.

Figure 5:
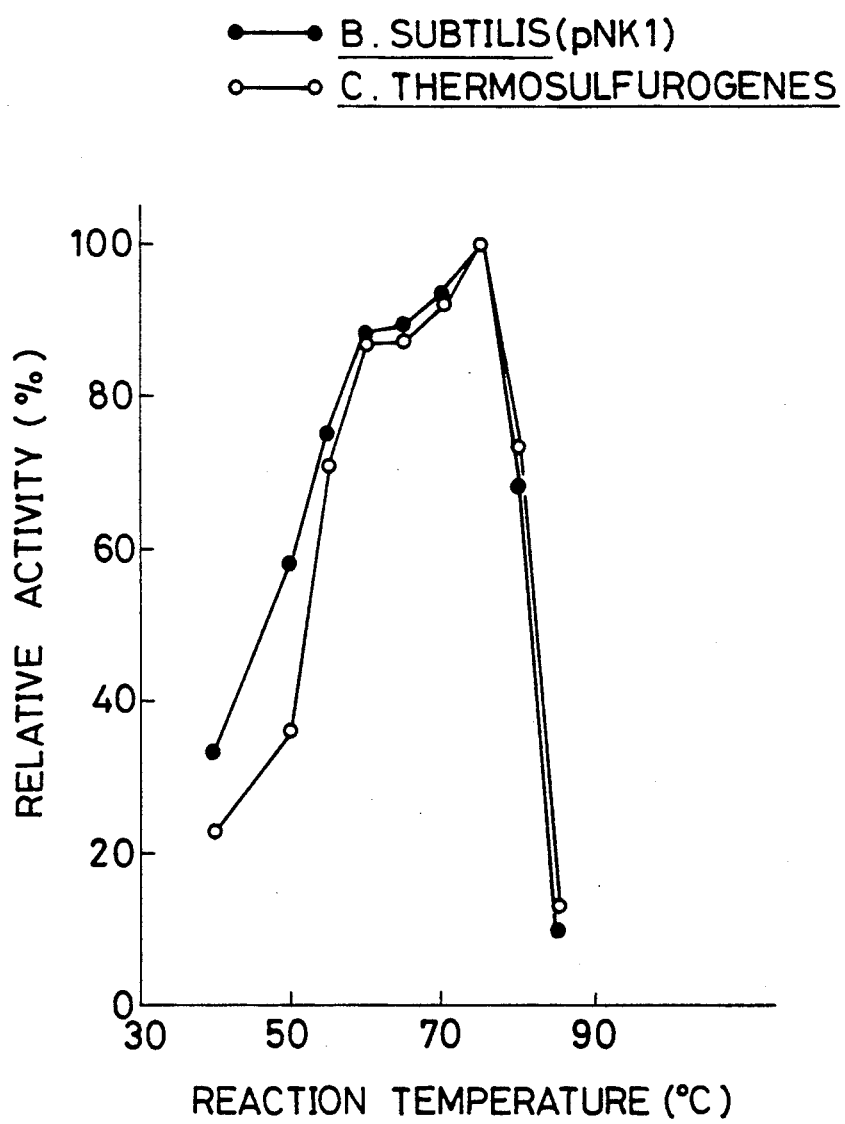
FIG. 5 shows effects of temperature on the enzyme activity.

The optimal temperature of the β-amylase from *C. thermosulfurogenes* was compared with that of the β-amylase obtained by the above mentioned cloned cells. As shown in FIG. 5, the relative activities of β-amylase from both cultures increased up to 75° C. and decreased remarkably over 75° C. Both of them had an optimal temperature of 75° C.

What we claim is:

1. A recombinant gene coding for a thermostable β-amylase having the following amino acid sequence:

*654 677*
Ser Ile Ala Pro Asn Phe Lys Val

*678
Phe Val Met Gly Pro Leu Glu Lys Val Thr

737*
Asp Phe Asn Ala Phe Lys Asp Gln Leu Ile

*738
Thr Leu Lys Asn Asn Gly Val Tyr Gly Ile

797*
Thr Thr Asp Ile Trp Trp Gly Tyr Val Glu

*798
Asn Ala Gly Glu Asn Gln Phe Asp Trp Ser

857*
Tyr Tyr Lys Thr Tyr Ala Asp Thr Val Arg

*858
Ala Ala Gly Leu Lys Trp Val Pro Ile Met

917*
Ser Thr His Ala Cys Gly Gly Asn Val Gly

*918
Asp Thr Val Asn Ile Pro Ile Pro Ser Trp

977*
Val Trp Thr Lys Asp Thr Gln Asp Asn Met

*978
Gln Tyr Lys Asp Glu Ala Gly Asn Trp Asp

1037*
Asn Glu Ala Val Ser Pro Trp Tyr Ser Gly

*1038
Leu Thr Gln Leu Tyr Asn Glu Phe Tyr Ser

1097*
Ser Phe Ala Ser Asn Phe Ser Ser Tyr Lys

*1098
Asp Ile Ile Thr Lys Ile Tyr Ile Ser Gly

1157*
Gly Pro Ser Gly Glu Leu Arg Tyr Pro Ser

*1158
Tyr Asn Pro Ser His Gly Trp Thr Tyr Pro

1217*
Gly Arg Gly Ser Leu Gln Cys Tyr Ser Lys

*1218
Ala Ala Ile Thr Ser Phe Gln Asn Ala Met

1277*
Lys Ser Lys Tyr Gly Thr Ile Ala Ala Val

*1278
Asn Ser Ala Trp Gly Thr Ser Leu Thr Asp

1337*
Phe Ser Gln Ile Ser Pro Pro Thr Asp Gly

1338*
Asp Asn Phe Phe Thr Asn Gly Tyr Lys Thr

1397*
Thr Tyr Gly Asn Asp Phe Leu Thr Trp Tyr

*1398
Gln Ser Val Leu Thr Asn Glu Leu Ala Asn

1457*
Ile Ala Ser Val Ala His Ser Cys Phe Asp

*1458
Pro Val Phe Asn Val Pro Ile Gly Ala Lys

1517*
Ile Ala Gly Val His Trp Leu Tyr Asn Ser

*1518
Pro Thr Met Pro His Ala Ala Glu Tyr Cys

1577*
Ala Gly Tyr Tyr Asn Tyr Ser Thr Leu Leu

*1578
Asp Gln Phe Lys Ala Ser Asn Leu Ala Met

1637*
Thr Phe Thr Cys Leu Glu Met Asp Asp Ser

*1638
Asn Ala Tyr Val Ser Pro Tyr Tyr Ser Ala

1697*
Pro Met Thr Leu Val His Tyr Val Ala Asn

*1698
Leu Ala Asn Asn Lys Gly Ile Val His Asn

1757*
Gly Glu Asn Ala Leu Ala Ile Ser Asn Asn

*1758
Asn Gln Ala Tyr Val Asn Cys Ala Asn Glu

1817*
Leu Thr Gly Tyr Asn Phe Ser Gly Phe Thr

*1818
Leu Leu Arg Leu Ser Asn Ile Val Asn Ser

1877*
Asp Gly Ser Val Thr Ser Glu Met Ala Pro

*1878
Phe Val Ile Asn Ile Val Thr Leu Thr Pro

1937*
Asn Gly Thr Ile Pro Val Thr Phe Thr Ile

*1938
Asn Asn Ala Thr Thr Tyr Tyr Gly Gln Asn

1997*
Val Tyr Ile Val Gly Ser Thr Ser Asp Leu

*1998
Gly Asn Trp Asn Thr Thr Tyr Ala Arg Gly

2057*
Pro Ala Ser Cys Pro Asn Tyr Pro Thr Trp

*2058
Thr Ile Thr Leu Asn Leu Leu Pro Gly Glu

2117*
Gln Ile Gln Phe Lys Ala Val Lys Ile Asp

*2118
Ser Ser Gly Asn Val Thr Trp Glu Gly Gly

2177*
Ser Asn His Thr Tyr Thr Val Pro Thr Ser

*2178
Gly Thr Gly Ser Val Thr Ile Thr Trp Gln.

2. The gene of claim 1, which is isolated and purified from *Clostridium thermosulfurogenes*.

3. A plasmid DNA comprising the gene described in claim 1 and a plasmid.

4. The plasmid DNA of claim 3 wherein the plasmid is a plasmid pHW 1-B.

5. A transformant which is a microorganism transformed with the plasmid DNA described in claim 4.

6. A process for producing thermostable β-amylase, which comprises cultivating the transformant of claim 5, whereby the plasmid acts as an expression vector to produce β-amylase, and isolating the β-amylase.

7. A transformant which is a microorganism transformed with the plasmid DNA described in claim 3.

8. The transformant of claim 7, wherein the microorganism is *B. subtilis*.

9. A process for producing thermostable β-amylase, which comprises cultivating the transformant of claim 7, whereby the plasmid acts as an expression vector to produce β-amylase, and isolating the β-amylase.

10. A recombinant gene coding for a thermostable β-amylase of the following nucleic acid sequence:

```
*654                         677*
AGC.ATA.GCA.CCA.AAT.TTC.AAA.GTT

*678
TTT.GTA.ATG.GGT.CCA.TTA.GAA.AAA.GTC.ACA.
                             737*
GAT.TTT.AAT.GCA.TTC.AAA.GAT.CAA.TTG.ATA

*738
ACT.TTA.AAG.AAT.AAT.GGT.GTT.TAT.GGT.ATA.
                             797*
ACA.ACA.GAT.ATT.TGG.TGG.GGC.TAT.GTT.GAA

*798
AAT.GCA.GGT.GAA.AAT.CAA.TTT.GAC.TGG.AGT.
                             857*
TAT.TAT.AAG.ACA.TAT.GCT.GAT.ACC.GTA.CGC

*858
GCT.GCG.GGA.TTG.AAG.TGG.GTT.CCA.ATA.ATG.
                             917*
TCA.ACG.CAT.GCC.TGT.GGA.GGT.AAT.GTT.GGT.

*918
GAT.ACA.GTA.AAT.ATA.CCT.ATT.CCG.TCA.TGG.
                             977*
GTA.TGG.ACA.AAA.GAT.ACC.CAA.GAT.AAT.ATG

*978
CAG.TAT.AAG.GAT.GAA.GCC.GGA.AAT.TGG.GAT.
                             1037*
AAT.GAA.GCA.GTA.AGT.CCA.TGG.TAT.TCT.GGC

*1038
TTA.ACC.CAA.CTC.TAT.AAT.GAA.TTT.TAT.TCA.
                             1097*
TCT.TTT.GCA.TCA.AAT.TTT.AGC.AGC.TAT.AAA

*1098
GAT.ATA.ATT.ACT.AAA.ATA.TAT.ATA.TCT.GGA.
                             1157*
GGC.CCT.TCT.GGA.GAA.TTA.AGA.TAT.CCT.TCA

*1158
TAT.AAT.CCT.TCG.CAT.GGA.TGG.ACA.TAT.CCT.
                             1217*
GGA.CGT.GGC.TCG.CTG.CAG.TGC.TAT.AGT.AAA

*1218
GCG.GCT.ATA.ACA.AGT.TTT.CAA.AAT.GCT.ATG.
                             1277*
AAG.TCT.AAA.TAT.GGA.ACT.ATA.GCA.GCA.GTT

*1278
AAT.AGT.GCA.TGG.GGT.ACA.AGC.CTA.ACT.GAT.
                             1337*
TTT.TGT.CAA.ATT.AGT.CCA.CCT.ACA.GAT.GGT

*1338
GAT.AAT.TTC.TTT.ACA.AAT.GGT.TAT.AAA.ACT.
                             1397*
ACT.TAT.GGT.AAT.GAC.TTT.TTG.ACA.TGG.TAT

*1398
CAA.AGT.GTT.TTG.ACT.AAT.GAG.TTA.GCC.AAT.
                             1457*
ATT.GCT.TCT.GTA.GCT.CAT.AGC.TGC.TTT.GAT

*1458
CCA.GTA.TTT.ATT.GTT.CCA.ATA.GGA.GCA.AAA.
                             1517*
ATA.GCT.GGA.GTG.CAT.TGG.CTA.TAT.AAT.AGT

*1518
CCG.ACA.ATG.CCA.CAT.GCT.GCA.GAA.TAT.TGT.
                             1577*
GCC.GGT.TAT.TAT.AAT.TAT.AGC.ACG.CTA.CTC

*1578
GAT.CAA.TTT.AAG.GCA.TCT.AAT.CTT.GCT.ATG.
                             1637*
ACA.TTT.ACA.TGT.CTT.GAA.ATG.GAT.GAT.TCT

*1638
AAT.GCA.TAT.GTA.AGT.CCA.TAT.TAT.TCT.GCA.
                             1697*
CCT.ATG.ACG.TTA.GTC.CAT.TAT.GTA.GCT.AAT

*1698
CTT.GCT.AAT.AAT.AAA.GGT.ATA.GTC.CAC.AAT.
                             1757*
GGA.GAA.AAT.GCT.TTG.GCT.ATA.TCC.AAC.AAC

*1758
AAT.CAA.GCT.TAT.GTG.AAT.TGT.GCA.AAT.GAA.
                             1817*
TTA.ACA.GGA.TAT.AAT.TTT.TCT.GGA.TTT.ACA

*1818
CTT.TTA.AGA.CTT.TCG.AAT.ATT.GTA.AAT.AGT.
                             1877*
GAT.GGA.TCT.GTG.ACA.TCA.GAG.ATG.GCT.CCT

*1878
TTT.GTA.ATT.AAT.ATA.GTT.ACA.CTA.ACG.CCT.
                             1937*
AAC.GGT.ACG.ATA.CCA.GTT.ACA.TTT.ACA.ATA

*1938
AAC.AAT.GCG.ACA.ACT.TAT.TAT.GGA.CAA.AAT.
                             1997*
GTA.TAT.ATT.GTT.GGT.AGT.ACA.TCT.GAT.CTT

*1998
GGA.AAT.TGG.AAT.ACA.ACC.TAT.GCC.CGT.GGT.
                             2057*
CCT.GCA.TCA.TGC.CCT.AAT.TAT.CCT.ACT.TGG

*2058
ACA.ATA.ACG.CTT.AAT.CTA.TTA.CCT.GGT.GAG.
                             2117*
CAG.ATA.CAG.TTT.AAA.GCT.GTA.AAA.ATT.GAT
```

-continued

*2118
AGT.TCA.GGA.AAT.GTA.ACT.TGG.GAA.GGT.GGC.

2177*
TCG.AAT.CAT.ACT.TAT.ACT.GTG.CCG.ACA.TCT

*2178
GGG.ACT.GGT.AGT.GTC.ACC.ATT.ACA.TGG.CAA.

11. The plasmid DNA comprising the gene described in claim 10 and a plasmid.

12. The plasmid DNA of claim 11 wherein the plasmid is plasmid pHW 1-8.

13. A transformant, which is a microorganism transformed with the plasmid DNA of claim 11.

14. The transformant of claim 13, wherein the microorganism is *B. subtilis.*

15. A process for producing thermostable β-amylase, which comprises cultivating the transformant of claim 14, whereby the plasmid acts as an expression vector to produce β-amylase, and isolating the β-amylase.

16. A plasmid DNA which is plasmid pNK1.

17. A transformant which is a microorganism transformed with plasmid pNK1.

18. The transformant of claim 17, wherein the microorganism is *B. subtilis.*

19. A process for producing thermostable β-amylase, which comprises cultivating the transformant of claim 17, whereby the plasmid acts as an expression vector to produce β-amylase, and isolating the β-amylase.

* * * * *